United States Patent
Behrends et al.

(10) Patent No.: US 8,404,261 B2
(45) Date of Patent: Mar. 26, 2013

(54) ANTIMICROBIALLY ACTIVE COMPOSITION HAVING A CONTENT OF BISPYRIDIUM ALKANE (OCTENIDINE DIHYDROCHLORIDE)

(75) Inventors: Sabine Behrends, Appen (DE); Boris Baur, Hamburg (DE); Thomas Spuida, Hamburg (DE); Andreas Dettmann, Hamburg (DE)

(73) Assignee: Air Liquide Sante (International), Paris (FR)

( * ) Notice: Subject to any disclaimer, the term of this patent is extended or adjusted under 35 U.S.C. 154(b) by 474 days.

(21) Appl. No.: 12/447,024

(22) PCT Filed: Oct. 23, 2007

(86) PCT No.: PCT/EP2007/061363
§ 371 (c)(1),
(2), (4) Date: Apr. 29, 2010

(87) PCT Pub. No.: WO2008/052912
PCT Pub. Date: May 8, 2008

(65) Prior Publication Data
US 2011/0076242 A1    Mar. 31, 2011

(30) Foreign Application Priority Data
Oct. 31, 2006  (DE) .......................... 10 2006 051 891

(51) Int. Cl.
*A01N 25/00*  (2006.01)
*A01N 25/34*  (2006.01)

(52) U.S. Cl. ...................................... 424/405; 424/404

(58) Field of Classification Search .................. None
See application file for complete search history.

(56) References Cited

U.S. PATENT DOCUMENTS

| 4,206,215 A | 6/1980 | Bailey |
| 4,420,484 A | 12/1983 | Gorman et al. |
| 6,258,370 B1 * | 7/2001 | Behrends et al. ............. 424/405 |
| 2005/0119313 A1 | 6/2005 | Behrends et al. |
| 2005/0169852 A1 | 8/2005 | Roberge et al. |
| 2006/0051385 A1 | 3/2006 | Scholz |

FOREIGN PATENT DOCUMENTS

| EP | 1192860 | | 4/2002 |
| EP | 1634942 | | 3/2006 |
| EP | 1634942 | A1 * | 3/2006 |
| GB | 1533952 | | 11/1978 |
| WO | 9820094 | | 5/1998 |
| WO | 9935012 | | 7/1999 |
| WO | 0202128 | | 1/2002 |
| WO | WO 0202128 | A2 * | 1/2002 |

OTHER PUBLICATIONS

Langer S, The impact of topical anticeptics on skin microcirculation, Eur. J. Med. Res., Sep. 29, 2004 vol. 9, No. 9, p. 4449-4454 (STN abstract made of record only).*
Search Report for PCT/EP2007/061363.
Chuanchuen, Rungtip et al., "Cross-Resistance Between Triclosan and Antibiotics in *Pseudomonas aeruginosa* Is Mediated by Multidrug Efflux Pumps: Exposure of a Susceptible Mutant Strain to Triclosan Selects nfxB Mutants Overexpressing MexCD-OprJ", Antimicrobial Agents and Chemotherapy, Feb. 2001, p. 428-432.
Written Opinion of PCT/EP2007/061363.

* cited by examiner

*Primary Examiner* — Sreeni Padmanabhan
*Assistant Examiner* — Svetlana M Ivanova
(74) *Attorney, Agent, or Firm* — Allen E. White

(57) ABSTRACT

A description is given according to the invention of a composition on an aqueous basis which comprises a) 0.001 to 10% by weight bispyridinium alkane, b) 0.1 to 30% by weight nonionic surfactant, c) 0 to 40% by weight aromatic alcohol and d) 0.01 to 10% by weight polyol selected from alkanediols and alkanetriols. The compositions, as mouthwash solutions, are more active than current commercial products and are distinguished by a pleasant taste and low tendency to foaming.

35 Claims, No Drawings

ANTIMICROBIALLY ACTIVE COMPOSITION HAVING A CONTENT OF BISPYRIDIUM ALKANE (OCTENIDINE DIHYDROCHLORIDE)

This application is a §371 of International PCT Application PCT/EP2007/061363, filed Oct. 23, 2007.

FIELD OF THE INVENTION

The present invention relates to an antimicrobially active composition on an aqueous basis which comprises a bispyridinium alkane, and also to the use of the composition as mouthwash solution or oral antiseptic.

BACKGROUND

There are a number of mouthwash solutions based on a variety of active compounds which are burdened with disadvantages. For example, the active compound chlorhexidine used in mouthwash solutions, in the case of long-term use, has the risk of side effects such as blackish-brown discolorations of the teeth, of plastic fillings and of the rear of the tongue, which must be removed by a professional mechanical teeth cleaning. Furthermore, interference with taste, desquamation and lesions to oral mucosa can occur. Interferences with wound healing are also described after immediate application post operationem.

In addition, anaphylactic reactions and hypersensitivities are reported. The period of use of chlorhexidine should not exceed 14 days on account of these known side effects.

Moreover, oral antiseptics based on polyvinylpyrrolidone-iodine (PVP-iodine) are known. Through their use, protein can lead to an effect on their activity. In addition, the colouring of the product leads to spots on textiles. In addition, there is a weak to absent residual activity of the product, and resorption of iodine or iodide. Contraindications which oppose the use of oral antiseptic based on PVP-iodine are diseases of the thyroid gland, pregnancy and lactation, as also known iodine sensitivity.

With products based on hexetidine, hypersensitivity reactions can occur. In addition, hexetidine is a formaldehyde-releasing compound which is of toxicological concern.

According to the prior art, in addition triclosan is known as an active compound for mouthwash solutions which induces resistance formation to important medicaments (see C. Rungtip, K. Beinlich, T. T. Hoang, A. Becher, R. R. Karkhoff-Schweizer, H. P. Schweizer, Cross-Resistance between Triclosan and Antibiotics in *Pseudomonas aeruginosa* Is Mediated by Multidrug Efflux Pumps: Exposure of a Susceptible Mutant Strain to Triclosan Selects nfxB Mutants Overexpressing MexCD-OprJ, Antimicrob. Agents and Chemother. 45 (2001) 428-432).

In addition, oral antiseptics are known based on the active compounds thymol, eucalyptol and menthol which are a toxicological concern, as phenolic compounds.

In addition, the use of compositions having a content of bispyridinium alkane (for example N,N'-(1,10-decanediyldi-1-[4H]-pyridinyl-4-ylidene)bis-(1-octanamine) dihydrochloride (hereinafter octenidine). Octenidine is a bispyridinium alkane having the following mesomeric limiting structures:

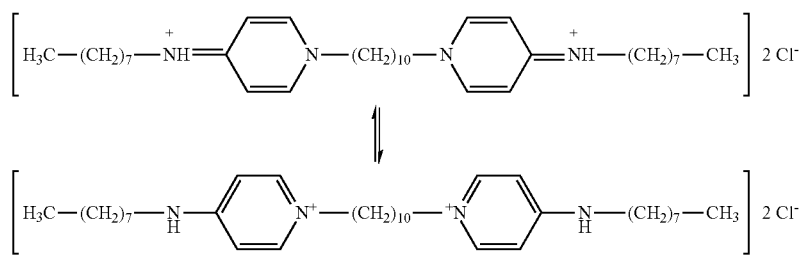

For instance, U.S. Pat. No. 4,206,215, describes the fact that bispyridinium alkanes can be used as antimicrobial agents, and especially as plaque-inhibiting dental care agents. WO 02/02128 discloses a topical oral composition for health promotion, which can contain octenidine. EP-A2-0 252 278 discloses a disinfectant and its use for skin and mucosal disinfection. The disinfectant is formulated on the basis of alcohol and hydrogen peroxide or a compound forming peroxide in aqueous phase and can contain octenidine.

EP-A1-0 411 315 discloses an aqueous antiseptic composition as mucosal antiseptic and for wound treatment which contains octenidine dihydrochloride and also phenoxyethanol and/or phenoxypropanol in defined amounts. The example formulations contain cocoamidopropyl betaine ((3-cocoamido-propyl)dimethylazaniumyl acetate), which leads to strong foaming which is unwanted for mouthwash solutions, or large amounts of fatty alcohols and silicone oil which, because of the fatty unpleasant taste, are disadvantageous for use in the oral cavity.

US 2006/0 051 385 A1 relates to cationic antiseptic compositions and use thereof. The compositions can contain octenidine according to the general disclosure. A specific teaching as to how octenidine-containing mouthwash solutions may be formulated cannot be taken from the disclosure document and it is not disclosed in the examples either.

Octenidine, in addition, has been successfully used for many years in the mucosal and wound antiseptic Octenisept® of the applicant. Disadvantages are the bitter taste and the foaming of the commercial product on gargling which impairs the suitability as mouthwash solution.

The object of the invention is accordingly to provide a composition which overcomes the described disadvantages of the prior art. In particular, a composition should be provided which

- is sufficiently taste-neutral or is of pleasant taste, that is for example does not have the bitter taste of octenidine,
- does not cause foaming on gargling,
- at low concentration of the active compound or the active compounds is sufficiently active against a broad microorganism spectrum, in particular is active against methicillin-resistant species of the type *Staphylococcus aureus* and *Enterococcus faecalis* and is toxicologically harmless, even in the event of relatively long term use.

SUMMARY OF THE INVENTION

An antimicrobially active composition that overcomes the disadvantages of the prior art has now surprisingly been found. The antimicrobially active composition on an aqueous basis comprises:
a) 0.001 to 10% by weight bispyridinium alkane,
b) 0.05 to 30% by weight nonionic surfactant,
c) 0 to 40% by weight aromatic alcohol and
d) 0.01 to 10% by weight polyol selected from alkanediols and alkanetriols.
Further optional components are
e) fruit acid and/or salt thereof,
f) flavourings and/or sweeteners, and/or
g) acid, base and/or buffer.

DETAILED DESCRIPTION OF THE INVENTION

The invention is based, inter alia, on the fact that it has been found that by using nonionic surfactants which do not adversely effect the activity of the bispyridinium alkane, a composition is obtained which does not foam on gargling and is neutral in taste. In addition, flavourings, which additionally contribute to a pleasant taste, are better soluble in the compositions according to the invention. In addition, compositions of the invention are very highly active against all organisms relevant for oral antiseptics and mouthwash solutions, with simultaneously very good compatibility and acceptance. For instance, it follows from the examples that compositions of the invention having an active compound content of only 0.1% by weight octenidine are more active than the commercial product Chlorhexamed Forte® containing 0.2% by weight chlorhexidine digluconate as active compound.
a) Bispyridinium Alkane Compositions of the invention contain at least one bispyridinium alkane. The expression bispyridinium alkane includes the bis[4-(substituted-amino)-1-pyridinium]alkanes disclosed in DE 27 08 331 C2 and DE 102 05 883 A1. While all statements on bispyridinium alkanes apply to the entire substance class, they apply in particular to octenidine which is preferred in all embodiments of the invention.

Particularly preferably, octenidine is used as component a).

Preferred concentrations of component a) are 0.01 to 1% by weight, preferably 0.03 to 0.5% by weight, more preferably 0.05 to 0.2% by weight, in particular 0.08 to 0.12% by weight, for instance 0.1% by weight.
b) Nonionic Surfactant The preferred nonionic surfactants which can be used in compositions according to the invention are selected from fatty alcohol polyalkoxylates, sorbitan fatty acid esters and polyoxyethylene sorbitan fatty acid esters, alkyl glycosides and alkoxylated (in particular ethoxylated) fatty acid monoglycerides, with fatty acid monoglyceride substituted by 5 to 100 ethoxy groups being preferred, in particular fatty acid monoglyceride substituted by 20 to 70 ethoxy groups, such as, for example, by about 40 ethoxy groups (that is macrogol glycerol hydroxystearate containing 40 ethylene oxide units, which is obtainable under the names Eumulgin HRE 40 PH® from Cognis and Cremophor RH 40® from BASF).

The alcohol polyalkoxylates also include fatty alcohol alkoxylates, for example isodecyl ethoxylates containing various fractions of ethylene oxide, isotridecyl ethoxylates, polyethylene glycol ethers of stearyl, lauryl and cetyl and oleyl alcohol. The alcohols can have been alkoxylated with ethylene oxide, propylene oxide or any desired mixtures of ethylene oxide and propylene oxide. Alcohol polyalkoxylates are known, inter alia, under the names Lutensol®, Marlipal®, Marlox®, Brij® and Plurafac®.

In addition, as nonionic surfactants, use is made of the sorbitan esters usually present as oleates, stearates, laurates and palmitates which are termed polysorbates (for example Tween®).

In addition, as nonionic surfactants, use is made of alkyl glycosides.

In this case a preferred amount of component b) is in the range from 0.1 to 20% by weight, or 0.2 to 15% by weight, preferably 0.3 to 10% by weight, in particular 0.4 to 8% by weight, such as 0.5 to 5% by weight, for example 0.7 to 2% by weight, for instance 1.0% by weight.
c) Aromatic Alcohol Aromatic alcohols used according to the invention are preferably selected from (i) aryloxyalkanols (glycol monoaryl ethers), (ii) arylalkanols and (iii) oligoalkanol aryl ethers.

(i) Aryloxyalkanols used according to the invention have the formula Ar—O—(CHR)$_n$—OH where R=independently H (for n>2) or $C_1$- to $C_6$-alkyl, with n being an integer, and preferably 2 to 10, more preferably 2 to 6, and in particular 2 or 3. Whereas the group Ar can be a nuclear-substituted or unsubstituted aryl group, unsubstituted aryl, for example, phenyl or naphthyl, is preferred. Example aryloxyalkanols used according to the invention are phenoxyethanol and phenoxypropanols. Preferred phenoxypropanols are 1-phenoxypropan-2-ol, 2-phenoxypropan-1-ol, or mixtures thereof, and also 3-phenoxypropan-1-ol.

(ii) Arylalkanols used according to the invention have the formula Ar—(CHR)—OH where R=independently H or $C_1$- to $C_6$-alkyl, with n being an integer, and preferably 1 to 10, more preferably 1 to 6, and in particular 1, 2, 3 or 4. While the group Ar can be a nuclear-substituted or unsubstituted aryl group, unsubstituted aryl, for example phenyl or naphthyl, is preferred. Example arylalkanols are 3-phenylpropan-1-ol, phenethyl alcohol, veratryl alcohol (3,4-dimethoxyphenylmethyl alcohol), benzyl alcohol and 2-methyl-1-phenyl-2-propanol. The (iii) oligoalkanol aryl ethers include, for example, phenoxy diethanol, triethanol and oligoethanol, and phenoxy dipropanol, tripropanol and oligopropanol.

Particularly preferably, component c) is phenoxyethanol.

Preferred amounts of component c) are in the range from 0.2 to 15% by weight, preferably 0.3 to 10% by weight, more preferably 0.4 to 8% by weight, in particular 0.5 to 7% by weight, such as 0.7 to 3% by weight, for example about 2.0% by weight.
d) Polyol Preferred polyols are selected from 1,2-propylene glycol, 1,3-propylene glycol, butane-1,4-diol, sorbitol, (hexane-1,2,3,4,5,6-hexyl) and glycerol, with glycerol being particularly preferred. Preferred amounts of component d) are 0.05 to 5% by weight, preferably 0.1 to 3% by weight, more preferably 0.2 to 2% by weight, in particular 0.25 to 1% by weight, such as 0.3 to 0.7% by weight, for example about 0.4% by weight.
e) Fruit Acid and/or Salt Thereof Compositions of the invention can in addition comprise e) 0.05 to 10% by weight of at least one fruit acid and/or a salt thereof. Suitable fruit acids are selected from citric acid, lactic acid, malic acid, tartaric acid, gluconic acid, fumaric acid and succinic acid, with sodium gluconate being particularly preferred. Preferred quantitative ranges of component e) are 0.1 to 5% by weight, preferably 0.2 to 3% by weight, more preferably 0.25 to 2% by weight, in particular 0 to 1% by weight, such as 0.3 to 0.7% by weight, for example about 0.4% by weight.

f) Flavouring and/or Sweetener

Compositions of the invention can in addition comprise f) 0.025 to 10% by weight flavouring and/or sweetener. Suitable sweeteners are selected from alitame, aspartame, dulcin, neohesperidin DC, stevioside, sucralose, suosan and thaumatin. Neohesperidin DC (neohesperidin dihydrochalcone; 1-(4-((2-O-[6-deoxy-α-L-mannopyranosyl]-β-D-glucopyranosoyl)oxy)-2,6-dihydroxyphenyl)-3-[3-hydroxy-4-methxoyphenyl]-1-propanone) is a compound having the following formula

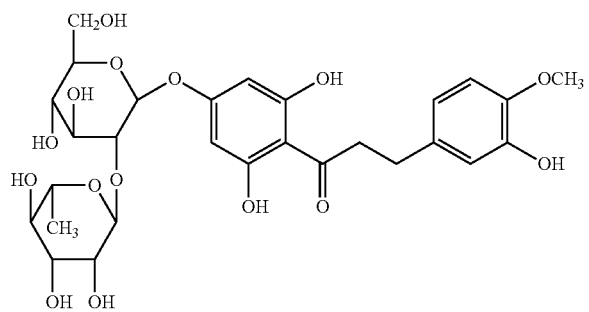

Neohesperidin D

Particular preference as sweetener is given to aspartame and/or neohesperidin DC.

Preferred flavourings are those which cover or mask well the bitter taste of bispyridinium alkane and are accepted well by the user.

g) Acid, Base and/or Buffer

Compositions of the invention can in addition comprise acid, base and/or buffer for setting the pH. It is preferred in this case that the component g) is present in an amount which sets the pH to 2 to 8, preferably 2.5 to 7, more preferably 3 to 6, such as 3.5 to 5, for example about 4.

Preferred weight ratios are
component a): flavouring—from 1:100 to 50:1, preferably 1:10 to 2:1;
component a): sweetener—1:200 to 5000:1, preferably 1:10 to 10:1;
flavouring: sweetener—1:20 to 1000:1, preferably 1:10 to 100:1.

Because compositions of the invention are present as aqueous solutions having a preferably high water content of at least 50% by weight, more preferably at least 60% by weight, in particular at least 70% by weight, such as at least 80% by weight, for example at least 90% by weight, e.g. at least 95% by weight water, they are typically single-phase and clear.

According to the invention, the presence of various components has proved to be not necessary or even disadvantageous. These components are therefore not present in compositions in preferred embodiments of the invention:

Preferably, according to the invention, compositions are free from quaternary ammonium compound, as is obligatorily prescribed according to US 2005/0 169 852 A1. In contrast to the bispyridinium alkanes present according to the invention, the conventional quaternary ammonium compounds such as for example cetylpyridinium chloride and benzalconium chloride lead to a severe foam development on gargling.

Preferred compositions according to the invention are free from hydrogen peroxide or peroxide-releasing compounds, as are obligatorily prescribed according to EP 0 252 278 A2. Disadvantages of peroxides are poor mucosal compatibility and limited stability in the formulation.

Compositions according to the invention are, in addition, preferably free from betaine and/or amine oxide, two active compound classes which are proposed according to U.S. Pat. No. 4,420,484 A1. Commercially conventional betaines, for example, cocoamidopropylbetaine, lead to undesirably vigorous foaming of aqueous compositions. In addition, it is assumed that the presence of amine oxides is accompanied by the occurrence of nitrosamines which are known as carcinogenic and are therefore of concern.

Compositions according to the invention are, in addition, preferably free from aldehydes as are obligatorily prescribed according to DE 42 01 391. Aldehydes are of toxicological concern.

Preferred preparations according to the invention are, in addition, free from silicone oils. Silicone oils typically have a low water solubility and their presence thus impedes the production of a single-phase composition.

Preferred compositions of the invention have a content of fatty alcohol of less than 10% by weight, such as less than 5% by weight, in particular less than 3% by weight, for example less than 1% by weight. In a particularly preferred embodiment, no fatty alcohol is present.

The invention in addition relates to the use of the antimicrobially active composition as mouthwash solution or oral antiseptic. The most important indications are:
antimicrobial mouthwashing before dental interventions and jaw surgery interventions;
prophylaxis and therapy of chemotherapy- or radiotherapy-induced muscositis;
improvement of oral cavity hygiene in immune-suppressed patients;
antimicrobial mouthwashing after accidental intake of infectious materials into the oral cavity;
before and possibly after operating interventions;
antimicrobial oral care in the case of jaw fractures with intermaxiallary immobilization;
root canal antisepsis;
treatment of caries and parodontosis;
implantology;
additional mouthwashing for daily routine oral hygiene in particular patient groups (for example immunosuppression);
reduction of plaque formation and prophylaxis of gingivitis in patients whose teeth cannot be cleaned manually;
before and during teeth treatment for reducing the microbial count in aerosols;
prevention or reduction of bacteraemia in patients at risk (for example endocarditis prophylaxis);
prevention of infections in intensive-care patients;
prevention of infections in patients under artificial respiration;
before intraoral injections and
treatment of carriers of multiresistant microorganisms in the oral cavity (for example MRSA).

In particular, the invention also relates to the use of the abovementioned components a) to d), and if appropriate e), f) and/or g) for producing a mouthwash solution, in particular for controlling MRSA and/or E. faecalis.

All indications can be used with a mouthwash solution and/or an oral antiseptic containing octenidine. Preference is given to treatment in the case of infection with multiresistant pathogens such as, for example, MRSA (methicillin-resistant *S. aureus*) and the treatment of parodontitis and the root canal. Comparisons of the efficacy on the organism *E. faecalis* important in root canal infections show that the formulation preferred according to the invention acts significantly better than Chlorhexamed Forte®.

The advantages of the invention follow, in particular, from the examples hereinafter.

EXAMPLES

Formulations

|  | 1 | 2 | 3 | 4 |
|---|---|---|---|---|
| Octenidine dihydrochloride | 0.10 | 0.10 | 0.10 | 0.10 |
| Cremophor RH 40 | 1.00 | 1.00 | 1.00 | 1.00 |
| Phenoxyethanol | 2.00 | 2.00 | 2.00 | 2.00 |
| Glycerol | 0.425 | 0.425 | 0.425 | 0.425 |
| Sodium gluconate | 0.40 | 0.40 | 0.40 | 0.40 |
| Flavouring | — | 0.25 | 0.25 | 0.25 |
| Neohesperidin DC | — | 0.02 | 0.02 | — |
| Aspartame powder | — | — | 0.20 | 0.20 |
| Citric acid | to pH 4 | to pH 4 | to pH 4 | to pH 4 |
| Purified water | to 100.00 | to 100.00 | to 100.00 | to 100.00 |

|  | 5 | 6 | 7 | 8 |
|---|---|---|---|---|
| Octenidine dihydrochloride | 0.05 | 0.10 | 0.20 | 0.20 |
| Cremophor RH 40 | 1.00 | 1.00 | 1.00 | 1.00 |
| Phenoxyethanol | — | — | — | 0.90 |
| Glycerol | 0.425 | 0.425 | 0.425 | 0.425 |
| Sodium gluconate | 0.40 | 0.40 | 0.40 | 0.40 |
| Flavouring | 0.25 | 0.25 | 0.25 | 0.25 |
| Aspartame powder | 0.20 | 0.20 | 0.20 | 0.20 |
| Citric acid | to pH 4 | to pH 4 | to pH 4 | to pH 4 |
| Purified water | to 100.00 | to 100.00 | to 100.00 | to 100.00 |

|  | 9 |
|---|---|
| Octenidine dihydrochloride | 0.10 |
| Eumulgin HRE 40PH | 1.00 |
| Phenoxyethanol | 2.00 |
| Glycerol | 0.425 |
| Sodium gluconate | 0.40 |
| Flavouring | 0.25 |
| Aspartame powder | 0.20 |
| Purified water | to 100.00 |

Example 1

Quantitative Suspension Experiment Using *E. Faecalis* (ATCC 19433)

Test Method Used: Extract from Standard Methods of the DGHM (German Society for Hygiene and Microbiology) for Testing Chemical Disinfection Methods, Sep. 1, 2001
9. Determination of the Bactericidal or Fungicidal Activity in a Quantitative Suspension Experiment
9.1 Quantitative Suspension Experiment Using Bacteria (Except for Mycobacteria) and Fungi
9.1.3 Methodology
9.1.3.1 Principle A sample of the product under test is provided with a bacterial or fungal suspension and this mixture is kept at the test temperature. After selected and determined times of action, an aliquot of the mixture is immediately neutralized by validated methods in order to investigate the bactericidal or fungicidal properties present. In each sample, the cell counts are determined and reduction therein is calculated. The method of choice is the dilution neutralization method. Only if a suitable neutralizing agent has not been found, may the membrane filtration method be used. The tests at relatively low or relatively high organic loading address use conditions of the preparation to be tested.
9.1.5 Evaluation Nutrient media are primarily evaluated where the amount of CFU (colony forming units) is between 15 and 300. The reduction factor (RF) is calculated according to the following formula:

$$Log_{10}RF = log_{10}(CFU\ col) - log_{10}(CFU\ D)$$

CFU col: count of CFU per ml without action of the product
CFU D: count of CFU per ml after action of the product In the test report, the CFU values must be listed per dilution stage, the $log_{10}$ (CFU D) and also the RF values must be tabulated.

Comparison of formulation 9 with a commercial product. Reduction factors are listed.

|  | Concn. (1) | 10 sec. | 15 sec. | 20 sec. | 30 sec. |
|---|---|---|---|---|---|
| Formulation 9 | 80% | 6.39 | 6.38 | 6.42 | 6.39 |
|  | 50% | 6.39 | 6.38 | 6.42 | 6.39 |
| Chlorhexamed forte ® | 80% | 0 | 1.91 | 2.22 | 3.98 |
|  | 50% | 0 | 0 | 0 | 0 |

(1) Concn. = Concentration

Result:

Formulation 9 containing only 0.1% of octenidine acts significantly better against the organism relevant for root canal treatments *Enterococcus faecalis* than the commercial product Chlorhexamed Forte® containing 0.2% chlorhexidine digluconate.

Example 2

Quantitative Suspension Experiment Using Various MRSA Isolates Under Dirty Conditions (Formulation 6)

The antimicrobial activity of formulation 6 against multiresistant *Staphylococcus aureus* isolates was tested. The antimicrobial activity was determined in quantitative suspension experiments under "dirty conditions" according to DGHM Methods Book 2001 (mhp Verlag, ISBN 3-88681-042-9). Times of action selected were 10, 20 and 30 seconds. The MRSA isolates used Nos. 740, 686 and 710 were provided by the Hygiene-Institut Hamburg.

The reduction factors are stated:

|  | Time | | |
|---|---|---|---|
| MRSA isolate | 10 sec. | 20 sec. | 30 sec. |
| MRSA No. 704 | 5.26 | 5.82 | >6.42 |
| MRSA No. 686 | 5.33 | >6.47 | >6.47 |
| MRSA No. 710 | 5.12 | 5.59 | >6.27 |

Result:

The octenidine-containing mouthwash solution, in the concentration tested, even at a time of action of 10 seconds, demonstrated a sufficient activity against all MRSA isolates used.

It will be understood that many additional changes in the details, materials and steps which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. An antimicrobially active composition on an aqueous basis which comprises
    a) 0.001 to 10% by weight bispyridinium alkane,
    b) 0.05 to 30% by weight nonionic surfactant,
    c1) at least 50% by weight water, and
    d) 0.01 to 10% by weight polyol, the polyol being selected from alkanediols and alkanetriols, and
    wherein the antimicrobially active composition
    is free from other quaternary ammonium compounds,
    is free from hydrogen peroxide or peroxide-releasing compounds,
    is free from betaine and/or amine oxide,
    is free from aldehydes and
    is free from silicone oils.

2. The composition of claim 1, wherein component a) is octenidine dihydrochloride.

3. The composition of claim 1, wherein the composition comprises from 0.01 to 1% by weight of component a).

4. The composition of claim 2, wherein the composition comprises from 0.03 to 0.5% by weight of component a).

5. The composition of claim 1, wherein the nonionic surfactant is selected from fatty alcohol polyalkoxylates, polysorbates, alkyl glycosides and alkoxylated fatty acid monoglycerides and mixtures thereof.

6. The composition of claim 2, wherein the nonionic surfactant is selected from fatty acid monoglyceride substituted by 5 to 100 ethoxy groups.

7. The component of claim 4, wherein the nonionic surfactant is selected from fatty acid monoglyceride substituted by from 20 to 70 ethoxy groups.

8. The composition of claim 1, wherein the composition comprises from 0.2 to 15% by weight of component b).

9. The composition of claim 2, wherein the composition comprises from 0.3 to 10% by weight of component b).

10. The composition of claim 4, wherein the composition comprises from 0.5 to 5% by weight of component b).

11. The composition of claim 1, further comprising an aromatic alcohol as a component c2) selected from i) aryloxyalkanols, ii) arylalkanols and iii) oligoalkanol aryl ethers and mixtures thereof.

12. The composition of claim 5, further comprising an aromatic alcohol as a component c2) selected from i) aryloxyalkanols, ii) arylalkanols and iii) oligoalkanol aryl ethers and mixtures thereof.

13. The composition of claim 11, wherein the aromatic alcohol of component c2) is phenoxyethanol.

14. The composition of claim 11, wherein the composition comprises from 0.2 to 15% by weight of component c2).

15. The composition of claim 11, wherein the composition comprises from 0.4 to 8% by weight of component c2).

16. The composition of claim 11, wherein the composition comprises from 0.7 to 3% by weight of component c2).

17. The composition of claim 1, wherein the polyol is selected from 1,2-propylene glycol, 1,3-propylene glycol, butane-1,4-diol, glycerol, sorbitol and mixtures thereof as component d).

18. The composition of claim 5, wherein the polyol is selected from 1,2-propylene glycol, 1,3-propylene glycol, butane-1,4diol, glycerol, sorbitol and mixtures thereof as component d).

19. The composition of claim 12, wherein the polyol is selected from 1,2-propylene glycol, 1,3-propylene glycol, butane-1,4-diol, glycerol, sorbitol and mixtures thereof as component d).

20. The composition of claim 2, wherein the polyol is glycerol as component d).

21. The composition of claim 1, wherein the composition comprises from 0.05 to 5% by weight of component d).

22. The composition of claim 2, wherein the composition comprises from 0.2 to 2% by weight of component d).

23. The composition of claim 12, wherein the composition comprises from 0.3 to 0.7% by weight of component d).

24. The composition of claim 1, wherein the composition further comprises e) from 0.05 to 10% by weight of a fruit acid, a fruit acid salt, or mixtures thereof.

25. The composition of claim 24, wherein the fruit acid is selected from citric acid, lactic acid, malic acid, tartaric acid, gluconic acid, fumaric acid and succinic acid and mixtures thereof as component e).

26. The composition of claim 1, wherein the composition further comprises from 0.05 to 10% by weight of a fruit acid as component e), the fruit acid being sodium gluconate.

27. The composition of claim 24, wherein the composition comprises from 0.05 to 5% by weight of component e).

28. The composition of claim 1, wherein the composition further comprises f) from 0.025 to 10% by weight flavoring, sweetener, or mixtures thereof.

29. The composition of claim 28, wherein the sweetener is selected from alitame, aspartame, dulcin, neohesperidin DC, stevioside, sucralose, suosan and thaumatin and mixtures thereof.

30. The composition of claim 25, wherein the composition further comprises from 0.025 to 10% by weight flavoring sweeteners or mixtures thereof, the sweetener when present being selected from aspartame, neohesperidin DC and mixtures thereof.

31. The composition of claim 1, wherein the composition further comprises g) an acid, a base, a buffer, or mixtures thereof.

32. The composition of claim 21, wherein component g) is present in an amount which sets the pH to 2 to 8.

33. The composition of claim 32, wherein component g) is present in an amount which sets the pH to 3 to 6.

34. A mouthwash solution comprising an antimicrobially active composition, said antimicrobially active composition including
    a) 0.001 to 10% by weight bispyridinium alkane,
    b) 0.05 to 30% by weight nonionic surfactant,
    c) 0 to 40% by weight aromatic alcohol and
    d) 0.01 to 10% by weight polyol, the polyol being selected from alkanediols and alkanetriols, and
    e) at least 50% by weight water, wherein the antimicrobial) active composition
    is free from quaternary ammonium compounds,
    is free from hydrogen peroxide or peroxide-releasing compounds,
    is free from betaine and/or amine oxide.
    is free from aldehydes and
    is free from silicone oils.

35. The mouthwash solution of claim 34, wherein the solution controls methicillin-resistant *S. aureus* and/or *E. faecalis*.

* * * * *